(12) United States Patent
Ando et al.

(10) Patent No.: US 12,651,669 B2
(45) Date of Patent: Jun. 9, 2026

(54) CHOLESTEROL RISK ESTIMATION DEVICE, CHOLESTEROL RISK ESTIMATION METHOD, AND COMPUTER PROGRAM

(71) Applicant: NISSIN FOODS HOLDINGS CO., LTD., Osaka (JP)

(72) Inventors: Noritaka Ando, Osaka (JP); Naohisa Shobako, Osaka (JP)

(73) Assignee: NISSIN FOODS HOLDINGS CO., LTD., Osaka (JP)

( * ) Notice: Subject to any disclaimer, the term of this patent is extended or adjusted under 35 U.S.C. 154(b) by 0 days.

(21) Appl. No.: 18/041,971

(22) PCT Filed: Mar. 28, 2022

(86) PCT No.: PCT/JP2022/015093
§ 371 (c)(1),
(2) Date: Feb. 16, 2023

(87) PCT Pub. No.: WO2022/270099
PCT Pub. Date: Dec. 29, 2022

(65) Prior Publication Data
US 2024/0266058 A1 Aug. 8, 2024

(30) Foreign Application Priority Data

Jun. 22, 2021 (JP) ................................. 2021-102923
Mar. 15, 2022 (JP) ................................. 2022-040635

(51) Int. Cl.
*G16H 50/30* (2018.01)
*A61B 5/00* (2006.01)
*A61B 5/145* (2006.01)

(52) U.S. Cl.
CPC ......... *G16H 50/30* (2018.01); *A61B 5/14542* (2013.01); *A61B 5/7221* (2013.01); *A61B 5/7267* (2013.01); *A61B 5/7275* (2013.01)

(58) Field of Classification Search
CPC ........ G16H 50/30; G16H 50/20; G16H 10/60; G16H 50/50
See application file for complete search history.

(56) References Cited

U.S. PATENT DOCUMENTS

2012/0328594 A1   12/2012   McKenna et al.
2015/0313516 A1   11/2015   Shimizu et al.
(Continued)

FOREIGN PATENT DOCUMENTS

JP     2007-127424 A     5/2007
JP     2013-509588 A     3/2013
(Continued)

OTHER PUBLICATIONS

Tsigalou, Christina, et al. "Estimation of low-density lipoprotein cholesterol by machine learning methods." Clinica Chimica Acta 517 (2021): 108-116. (Year: 2021).*
(Continued)

*Primary Examiner* — Jason B Dunham
*Assistant Examiner* — Constantine Siozopoulos
(74) *Attorney, Agent, or Firm* — Sughrue Mion, PLLC

(57) ABSTRACT

Conventionally, it has been necessary to collect blood of a subject and perform biochemical analysis to measure LDL cholesterol and HDL cholesterol. However, in this method, a needle or the like needs to be invasively inserted into the skin of the subject, which causes a psychological or physical burden on the subject. According to the present invention, it is possible to non-invasively estimate cholesterol based on attribute information and/or non-invasive biological information of a predetermined user by generating a cholesterol
(Continued)

estimation model by machine learning based on attribute information, non-invasive biological information, and blood examination data acquired from a plurality of subjects in advance.

12 Claims, 10 Drawing Sheets

(56) References Cited

U.S. PATENT DOCUMENTS

| | | | |
|---|---|---|---|
| 2017/0003297 A1 | 1/2017 | McKenna et al. | |
| 2018/0024143 A1 | 1/2018 | McKenna et al. | |
| 2019/0110720 A1 | 4/2019 | Shimizu et al. | |
| 2020/0321129 A1 | 10/2020 | Tanaka et al. | |
| 2021/0045640 A1* | 2/2021 | Poltorak | A61B 5/6847 |
| 2022/0051773 A1* | 2/2022 | Appelbaum | G16H 10/40 |

FOREIGN PATENT DOCUMENTS

| | | |
|---|---|---|
| JP | 2018-88263 A | 6/2018 |
| JP | 2020-162834 A | 10/2020 |
| WO | 2014/087825 A1 | 6/2014 |
| WO | 2017/204233 A1 | 11/2017 |
| WO | 2021/084375 A1 | 5/2021 |
| WO | WO-2022162660 A1 * | 8/2022 |

OTHER PUBLICATIONS

Alexeev, et al., "EIS System in adjunct to Treatments' monitoring and to diagnosis with the conventional methods", Mar. 2010, Summary of Clinical Investigations ES Teck Complex system, 8 pages total.

Chua, et al., "Investigation of Attention Deficit/Hyperactivity Disorder Assessment Using Electro Interstitial Scan Based on Chronoamperometry Technique", 2019, IEEE Access, vol. 7, doi: 10.1109/ACCESS.2019.2938095, 12 pages total.

Maarek, "Electro interstitial scan system: assessment of 10 years of research and development", 2012, Medical Devices: Evidence and Research, vol. 5, doi: 10.2147/MDER.S29319, 8 pages total.

Search Report (PCT/ISA/210) issued Jun. 7, 2022 by the International Searching Authority for International Patent Applicatin No. PCT/JP2022/015093.

Written Opinion (PCT/ISA/237) issued Jun. 7, 2022 by the International Searching Authority for International Patent Applicatin No. PCT/JP2022/015093.

Milan Vrbaski et al., "Lipid profile prediction based on artificial neural networks", Journal of Ambient Intelligence and Humanized Computing, vol. 14, No. 11,Jun. 24, 2019, pp. 15523-15533, https://link.springer.com/article/10.1007/S12652-019-01374-3/fulltext.html>.

W. B. Kannel et al., "A general cardiovascular risk profile: The Framingham study", American Journal of Cardiology, Cahners Publishing Co., Newton, MA, US, vol. 38, No. 1, Jul. 1, 1976, pp. 46-51.

Anonymous, "High cholesterol", Symptoms and causes, Mayo Clinic, Jun. 14, 2021, 5 pages, https://web.archive.org/web/20210614134023/https://www.mayoclinic.org/diseases-conditions/high-blood-cholesterol/symptoms-causes/syc-20350800.

European Extended Search Report issued Mar. 19, 2025 by the European Patent Office for EP Patent Application No. 22828018.6.

* cited by examiner

FIG. 2

| ELECTRODE | DIRECTION | ELECTRODE |
|---|:---:|---|
| 1   LEFT FOREHEAD | ↔ | 2   LEFT HAND |
| 3   RIGHT FOREHEAD | ↔ | 4   RIGHT HAND |
| 5   LEFT HAND | ↔ | 6   LEFT FOOT |
| 7   RIGHT HAND | ↔ | 8   RIGHT FOOT |
| 9   LEFT FOREHEAD | ↔ | 10   RIGHT FOREHEAD |
| 11   LEFT HAND | ↔ | 12   RIGHT HAND |
| 13   LEFT FOOT | ↔ | 14   RIGHT FOOT |
| 15   RIGHT HAND | ↔ | 16   LEFT FOREHEAD |
| 17   LEFT HAND | ↔ | 18   RIGHT FOREHEAD |
| 19   RIGHT FOOT | ↔ | 20   LEFT HAND |
| 21   LEFT FOOT | ↔ | 22   RIGHT HAND |

CHOLESTEROL RISK ESTIMATION DEVICE, CHOLESTEROL RISK ESTIMATION METHOD, AND COMPUTER PROGRAM

CROSS REFERENCE TO RELATED APPLICATIONS

This application is a National Stage of International Application No. PCT/JP2022/015093 filed on Mar. 28, 2022, claiming priority from Japanese Patent Application No. 2021-102923 filed on Jun. 22, 2021, and Japanese Patent Application No. 2022-040635 filed on Mar. 15, 2022, the disclosures of which are incorporated herein in their entirety by reference.

TECHNICAL FIELD

The present invention relates to a cholesterol risk estimation device, a cholesterol risk estimation method, and a computer program.

BACKGROUND ART

Lipoprotein contained in blood can be classified into four kinds of chylomicron, very low density lipoprotein (VLDL), low density lipoprotein (LDL) cholesterol, and high density lipoprotein (HDL) cholesterol.

The HDL cholesterol is also referred to as good cholesterol, as it is typically known that the risk of diseases such as arteriosclerosis increases when the HDL cholesterol is insufficient in blood. According to determination criteria at a blood examination, which are set by JAPAN SOCIETY OF NINGEN DOCK, the HDL cholesterol equal to or higher than 40 mg/dL is determined to be normal and the HDL cholesterol lower than 40 mg/dL is determined to be risky.

The LDL cholesterol is also referred to as bad cholesterol, as it is typically known that the risk of diseases such as arteriosclerosis increases when a large amount of the LDL cholesterol is present in blood. According to determination criteria at a blood examination, which are set by JAPAN SOCIETY OF NINGEN DOCK, the LDL cholesterol lower than 120 mg/dL is determined to be normal and the LDL cholesterol equal to or higher than 120 mg/dL is determined to be risky.

Conventionally, it has been necessary to collect blood of a subject and perform biochemical analysis to measure LDL cholesterol and the HDL cholesterol. However, in this method, a needle or the like needs to be invasively inserted into the skin of the subject, which causes a psychological or physical burden on the subject. A method disclosed in Patent Literature 1 has been known as a method of non-invasively measuring lipid as the whole lipoprotein.

CITATION LIST

Patent Literature

Patent Literature 1
International Publication No. WO 2014-087825

Non Patent Literature

Non Patent Literature 1
Psychology Research and Behavior Management 2011:4 81-86, Summary of the clinical investigations E. S. Teck Complex Mar. 20, 2010 Overview Non Patent Literature 2
R. N. Chua, Y. W. Hau, C. M. Tiew and W. L. Hau, "Investigation of Attention Deficit/Hyperactivity Disorder Assessment Using Electro Interstitial Scan Based on Chronoamperometry Technique", in IEEE Access, vol. 7, pp. 144679-144690, 2019, doi: 10.1109/AC-CESS.2019.2938095.
Non Patent Literature 3
Maarek A., Electro interstitial scan system: assessment of 10 years of research and development. Med Devices (Auckl). 2012; 5:23-30. doi:10.2147/MDER.S29319

SUMMARY OF INVENTION

Technical Problem

However, with the method disclosed in Patent Literature 1, it is impossible to estimate concentration for each of the kinds of lipoprotein such as LDL and HDL, and it is difficult to determine existence of health risk for each of LDL cholesterol and HDL cholesterol.

The present invention is made in view of the above-described situation and is intended to provide a cholesterol risk estimation device, a cholesterol risk estimation method, and a computer program that are capable of extremely accurately estimating health risk of cholesterol, in other words, LDL cholesterol or HDL cholesterol based on non-invasive biological information.

Solution to Problem

A cholesterol risk estimation device according to the present invention includes an information acquisition unit configured to acquire attribute information and non-invasive biological information of a predetermined user, an estimation model storage unit configured to store a cholesterol risk estimation model, and an estimation processing unit configured to calculate a cholesterol risk estimated value of the predetermined user based on the attribute information and/or the non-invasive biological information of the predetermined user by using the cholesterol risk estimation model.

The cholesterol risk estimation device according to the present invention further includes a training data storage unit configured to store a training data set, and a learning processing unit configured to generate the cholesterol risk estimation model by machine learning based on the training data set.

The attribute information includes any one or a combination of age and sex, and the non-invasive biological information includes any one or a combination of BMI, blood pressure, pulse wave data, electrocardiogram data, and biological impedance.

The training data set includes attribute information, non-invasive biological information, and a blood-measured cholesterol measured value of a subject.

The non-invasive biological information further includes oxygen saturation (SpO2).

Estimation accuracy of the cholesterol risk estimated value is accuracy at which risk presence can be classified with ROC_AUC of 0.7 or larger.

The learning processing unit provides labels indicating existence of the cholesterol risk to the training data set based on the blood-measured cholesterol measured value, and when a difference between the numbers of pieces of data with the cholesterol risk and data without the cholesterol risk among the labels is equal to or larger than a predetermined value, the learning processing unit increases the number of pieces of sample data in the training data set to reduce the difference.

The learning processing unit generates a first cholesterol risk estimation model and a second cholesterol risk estimation model by machine learning based on each of training data sets of different kinds, and the estimation processing unit calculates the cholesterol risk estimated value of the predetermined user by using the first cholesterol risk estimation model and the second cholesterol risk estimation model.

The cholesterol risk estimation device according to the present invention further includes a biological information estimation unit configured to estimate at least one piece or more of biological information among BMI, blood pressure, pulse wave data, electrocardiogram data, biological impedance, and oxygen saturation included in the biological information, and the information acquisition unit acquires, as biological information of the predetermined user, the biological information estimated by the biological information estimation unit.

A non-invasive cholesterol risk estimation system includes the cholesterol risk estimation device, and a biological information measurement device configured to measure non-invasive biological information.

A cholesterol risk estimation method according to the present invention includes a step of storing a training data set including attribute information, non-invasive biological information, and a blood-measured cholesterol measured value of a subject, a step of generating the cholesterol risk estimation model by machine learning based on the training data set, and a step of calculating a cholesterol risk estimated value of the predetermined user based on the attribute information and/or non-invasive biological information of the predetermined user by using the cholesterol risk estimation model.

A computer program according to the present invention causes a computer to execute a step of storing a training data set including attribute information, non-invasive biological information, and a blood-measured cholesterol measured value of a subject, a step of generating the cholesterol risk estimation model by machine learning based on the training data set, and a step of calculating a cholesterol risk estimated value of the predetermined user based on the attribute information and/or non-invasive biological information of the predetermined user by using the cholesterol risk estimation model.

Advantageous Effects of Invention

According to the present invention, it is to provide a cholesterol risk estimation device, a cholesterol risk estimation method, and a computer program that are capable of extremely accurately estimating cholesterol, in other words, a health risk of LDL cholesterol or HDL cholesterol by machine learning by using non-invasive biological information.

BRIEF DESCRIPTION OF DRAWINGS

FIG. 2 is a diagram for description of an electroscangram (ESG).

4

Figure 4:
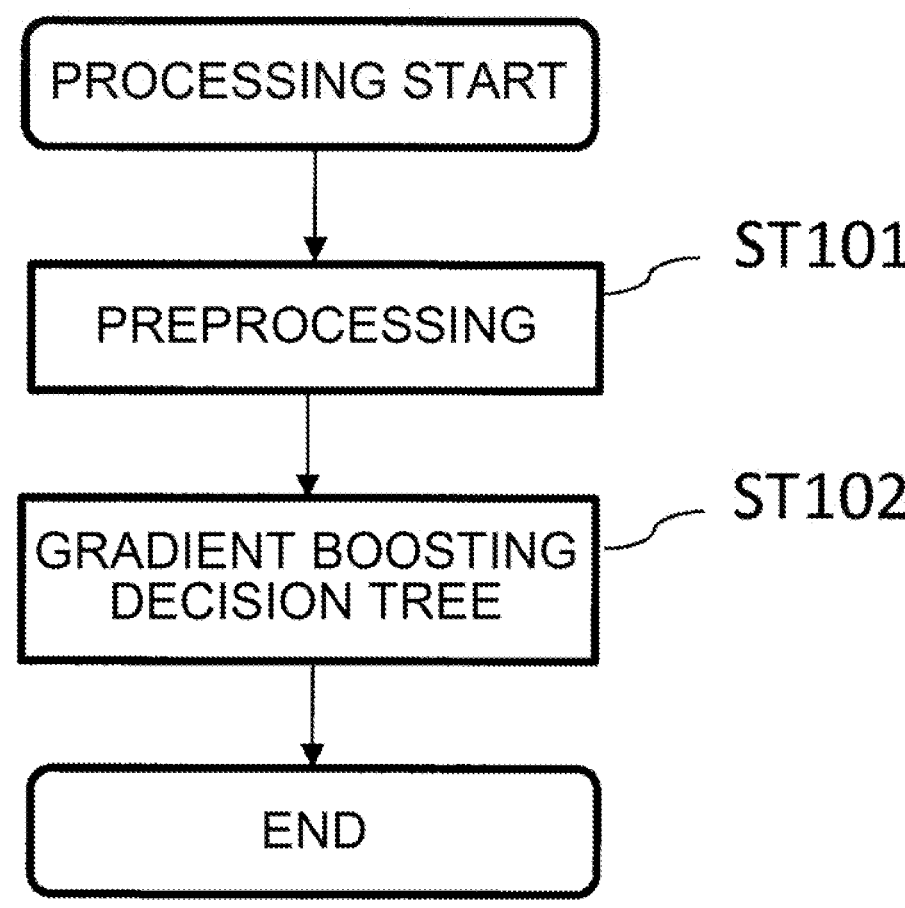

FIG. 4 is a flowchart illustrating an execution procedure of generation of an LDL cholesterol risk estimation model by machine learning.

Figure 5:
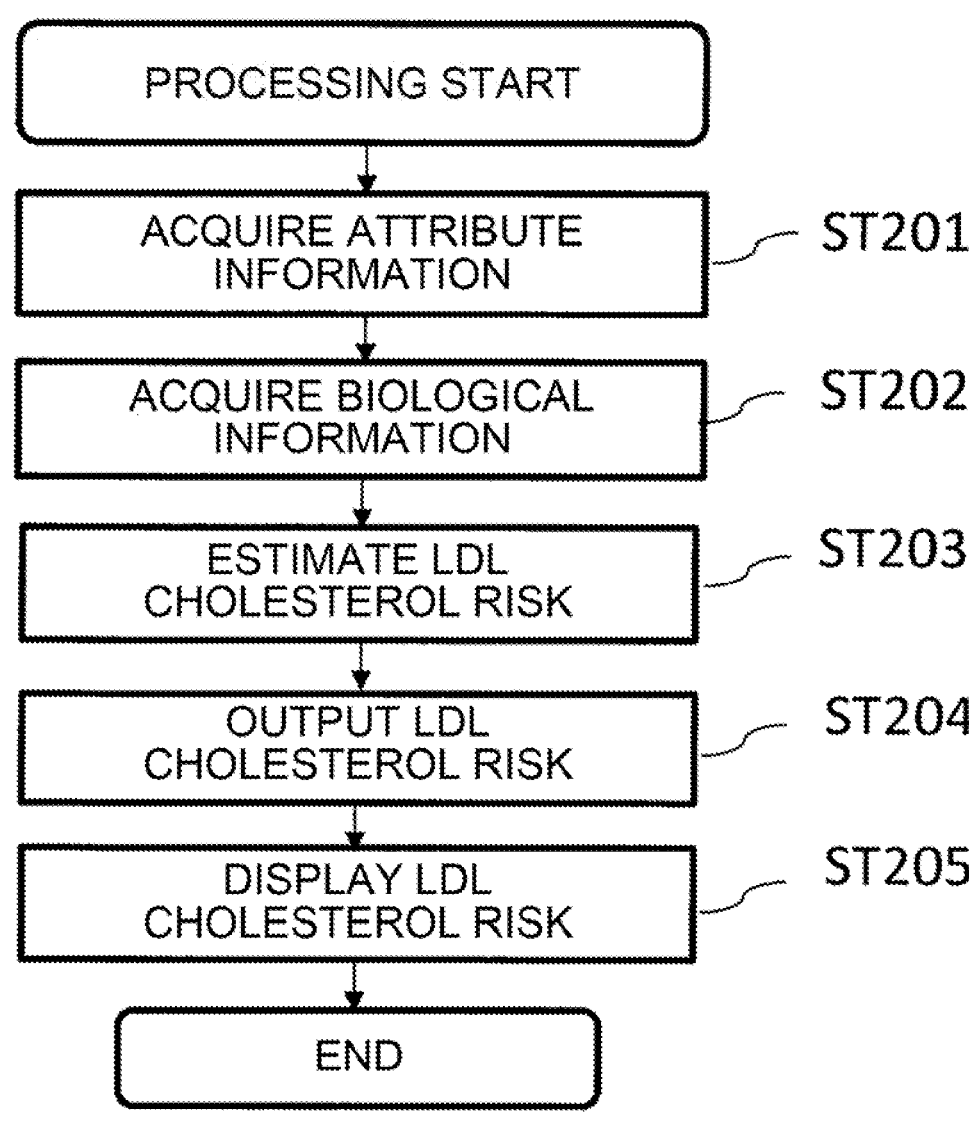

FIG. 5 is a flowchart illustrating the execution procedure of LDL cholesterol risk estimation processing.

Figure 6:
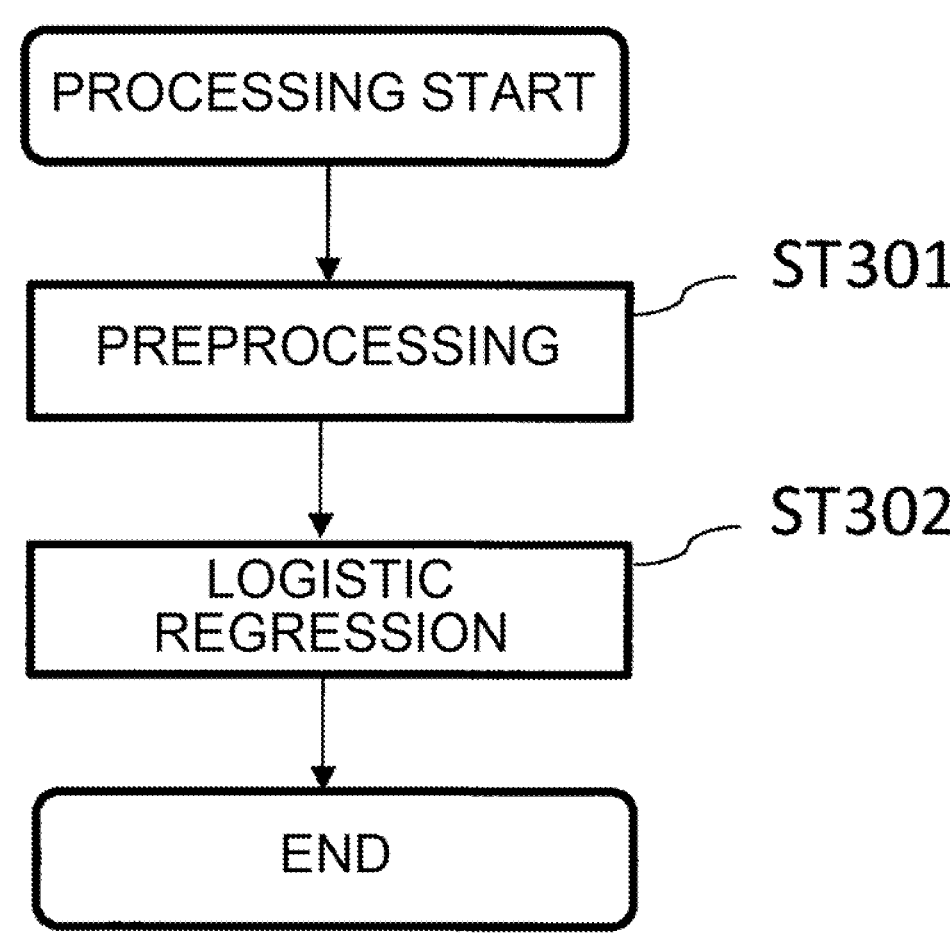

FIG. 6 is a flowchart illustrating an execution procedure of generation of an HDL cholesterol risk estimation model by machine learning.

Figure 7:
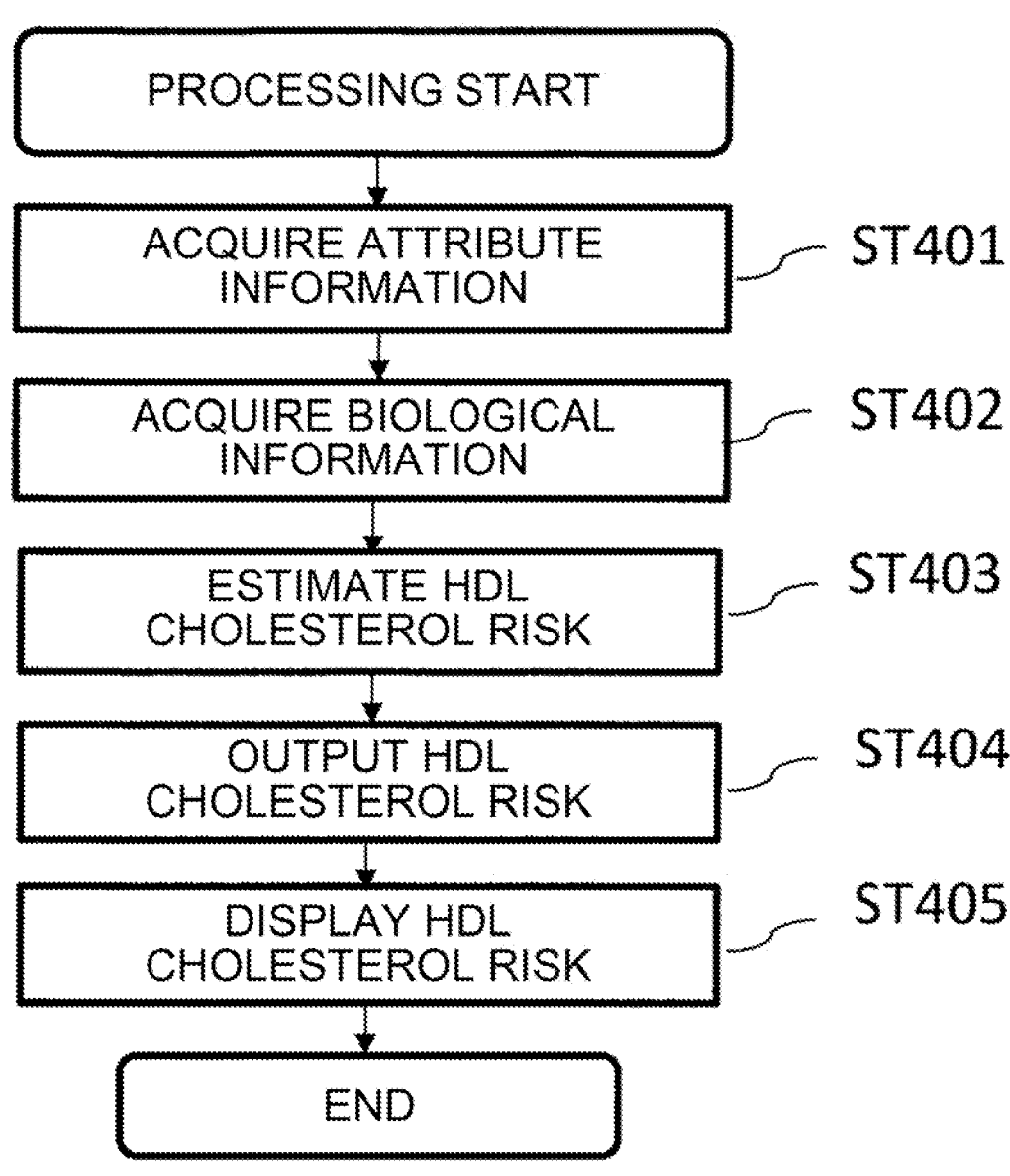

FIG. 7 is a flowchart illustrating the execution procedure of HDL cholesterol risk estimation processing.

Figure 8:
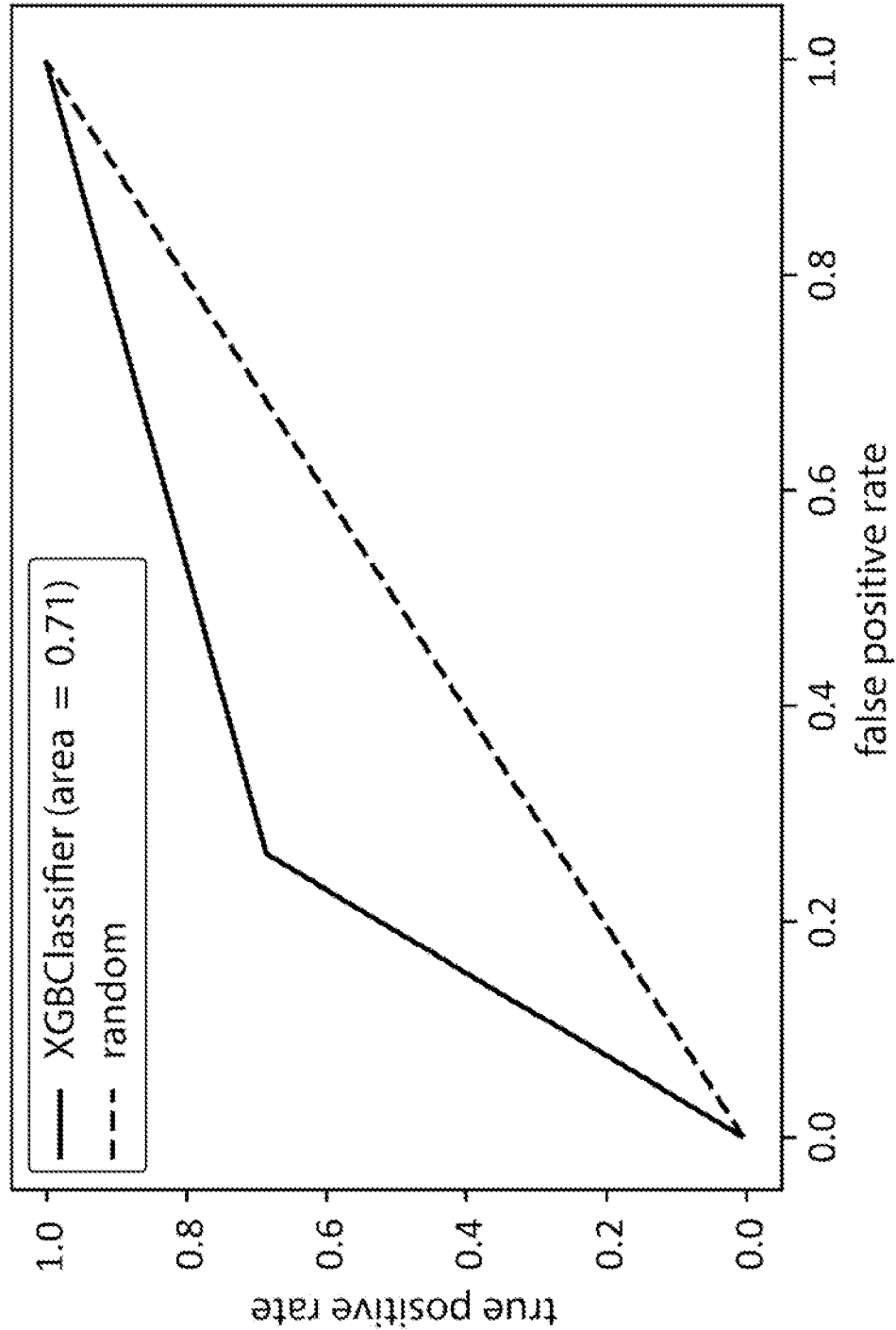

FIG. 8 illustrates an ROC_AUC curve of an estimation result in Example 1.

Figure 9:
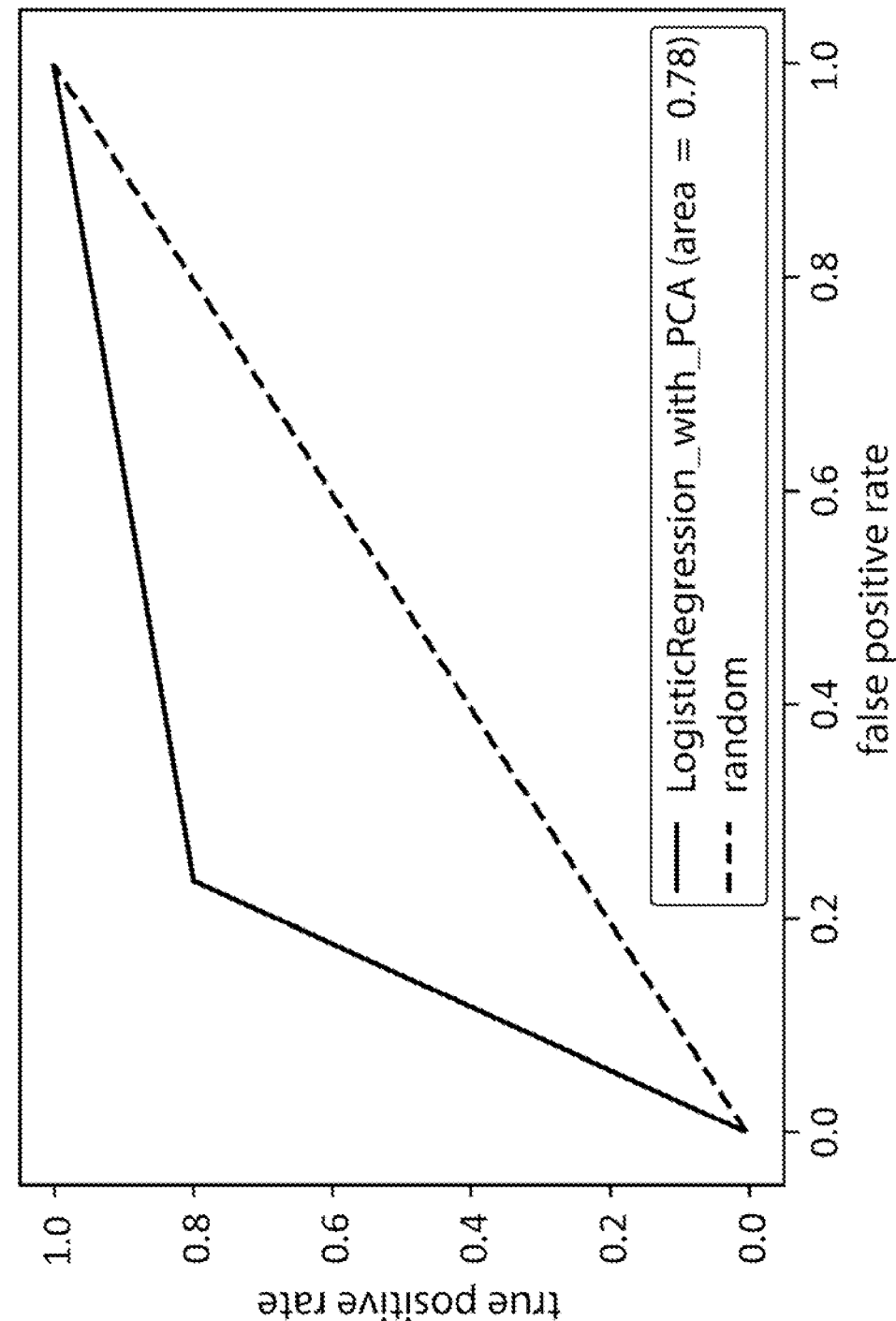

FIG. 9 illustrates an ROC_AUC curve of an estimation result in Example 2.

Figure 10:
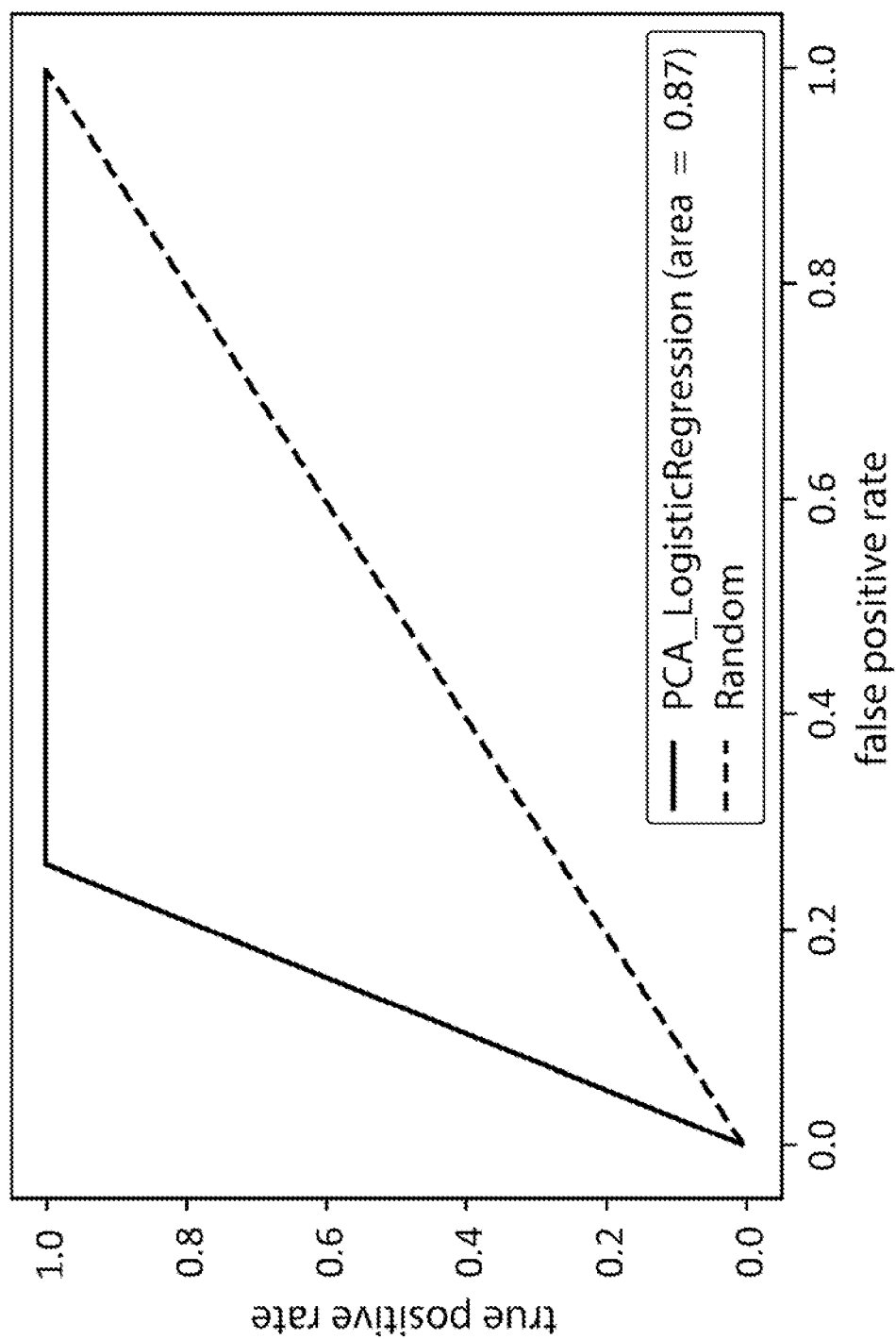

FIG. 10 illustrates an ROC_AUC curve of an estimation result in Example 3.

DESCRIPTION OF EMBODIMENT

An embodiment will be described below with reference to the accompanying drawings. Note that the embodiment is exemplary and the present invention is not limited to configurations described below.

<Device Functions>

Figure 1:
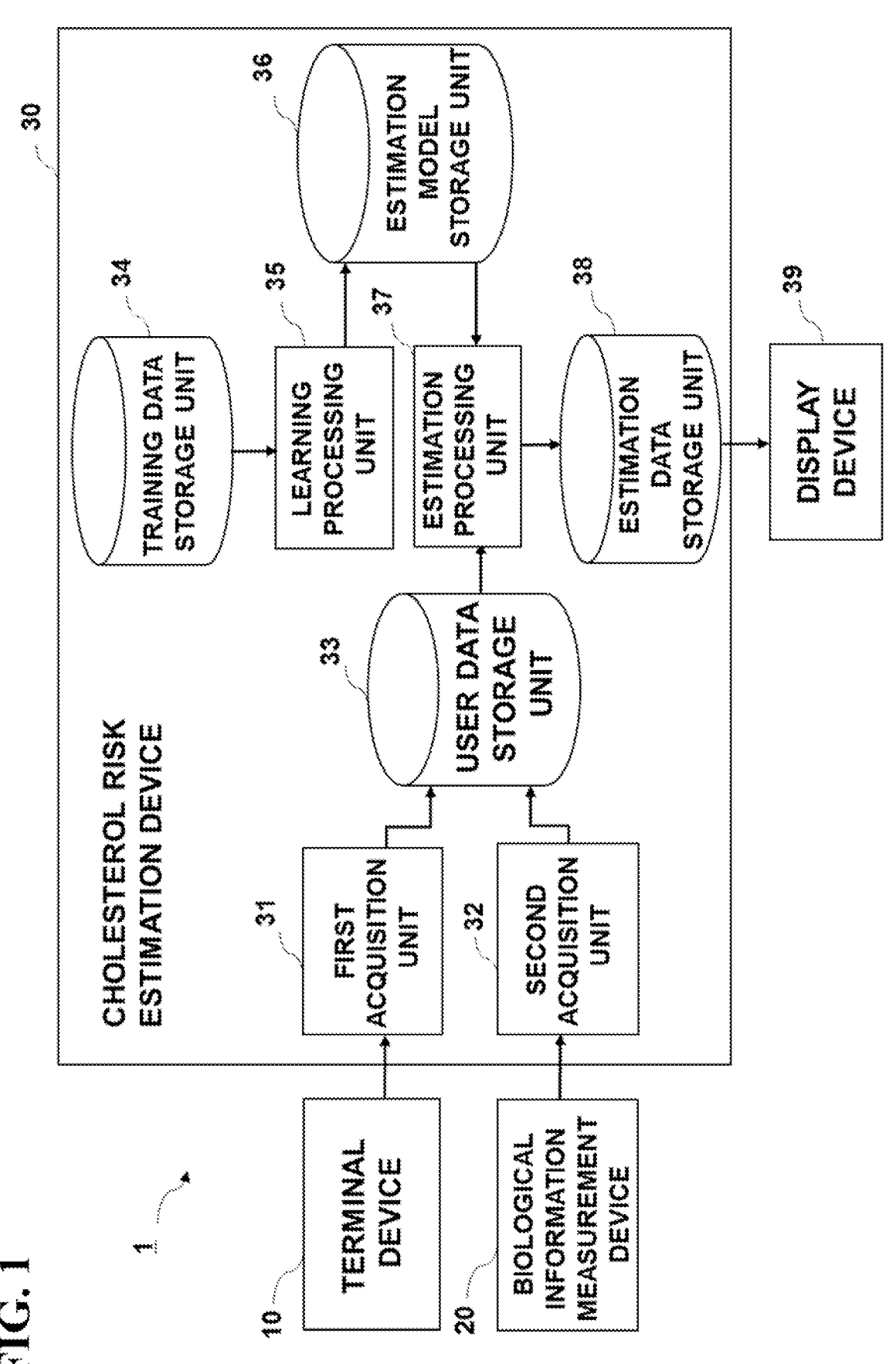
FIG. 1 is a block diagram illustrating a schematic configuration of a cholesterol risk estimation system.

A cholesterol risk estimation system 1 and a cholesterol risk estimation device 30 according to the present embodiment will be described below with reference to FIGS. 1 to 7. FIG. 1 is a block diagram illustrating a schematic configuration of the cholesterol risk estimation system 1 according to the present embodiment. The cholesterol risk estimation system 1 includes a terminal device 10, a biological information measurement device 20, the cholesterol risk estimation device 30, and a display device 39.

A "user" is a person who uses the cholesterol risk estimation system to non-invasively obtain an estimated value of the cholesterol risk. A "subject" is a person who provides, upon a predetermined procedure and an agreement, attribute information such as age or sex, non-invasive biological information, and a blood-measured cholesterol measured value as a training data set to be used in the cholesterol risk estimation system.

The terminal device 10 may be any information terminal to which the attribute information (such as full name, ID, age, or sex) of the user can be input and that can output the input information to the cholesterol risk estimation device 30 through a wired or wireless communication network. Examples of the terminal device 10 include portable terminals including a tablet terminal, a smartphone, and a wearable terminal, and include a personal computer (PC). Note that, height, weight, or the like may be measured by the biological information measurement device 20 to be described later.

The biological information measurement device 20 measures the non-invasive biological information of the user. The non-invasive biological information is biological information acquired by a method that does not require insertion of an instrument into the skin or an opening part of the body. The non-invasive biological information may be measured by using, for example, a commercially available height meter, weight meter, blood pressure meter, pulse oximeter, pulse wave meter, electrocardiogram meter, impedance measurement machine, or galvanic skin measurement machine. Alternatively, ES-TECK BC-3 (Ryobi Systems Co., Ltd.) that can simultaneously measure pulse wave data, electrocardiogram data, biological impedance, and oxygen saturation (SpO2) may be used. These devices can measure non-invasive biological data without providing a psychological nor physical load on the user.

In the embodiment of the present invention, the non-invasive biological information includes any one or a combination of the body mass index (BMI), blood pressure, pulse wave data, electrocardiogram data, and biological impedance and may further include oxygen saturation (SpO2).

The BMI is calculated by the following formula based on a height h [m] and a weight w [kg].

$$BMI = w/h^2 \left[ kg/m^2 \right]$$

The blood pressure includes any one or a combination of systolic blood pressure, diastolic blood pressure, pulse pressure, and average arterial blood pressure.

The pulse pressure is calculated by the following expression.

$$Pulse \ pressure = systolic \ blood \ pressure - diastolic \ blood \ pressure$$

The average arterial blood pressure is calculated by the following expression.

$$Average \ arterial \ blood \ pressure = $$
$$diastolic \ blood \ pressure + pulse \ pressure \times 1/3$$

The pulse wave data is obtained by irradiating, by using a sphygmograph or a pulse oximeter, a protruding body site such as a finger with red light (up to 660 nm) from a red LED and with near-infrared light (up to 905 nm) from an IR LED and measuring transmitted light thereof by using a phototransistor.

The pulse wave data includes any one or a combination of pulse, the elasticity index, the peripheral vascular resistance, the acceleration plethysmogram, b/a, e/a, -d/a, the Takazawa's second derivative of photoplethysmogram aging index, the ejection fraction, the LVET, and the dicrotic elasticity index (DEI).

The elasticity index is a numerical value obtained by dividing the height by the time from detection of a systolic peak to detection of a diastolic peak in the photoplethysmogram. The peripheral vascular resistance is calculated by "average arterial blood pressure"/"cardiac output"×80. The dicrotic elasticity index (DEI) is an indicator of the diastolic vascular elasticity and can be measured by a PWV measurement device. The DEI of 0.3 to 0.7 is normal, the DEI of 0.3 or lower indicates the possibility of high-blood pressure or arteriosclerosis, and the DEI of 0.7 or higher indicates the possibility of acute anxiety neurosis.

The acceleration plethysmogram is the second derivative of photoplethysmogram (PTG) (SDPTG). The acceleration plethysmogram is constituted by the initial positive wave (a wave), the initial negative wave (b wave), the mesosystolic re-elevation wave (c wave), the late systolic re-descent wave (d wave), and the early diastolic positive wave (e wave), and b/a, e/a, and −d/a are calculated from ratios of the heights of the waves. It is observed that b/a increases and c/a, d/a, and e/a decrease along with aging, and thus aging of blood vessels can be evaluated by the Takazawa's second derivative of photoplethysmogram aging index (b–c–d–e)/a. The ejection fraction is the ratio of blood transferred from the ventricles at each heartbeat and is proportional to the second derivative of photoplethysmogram aging index. The LVET is the left ventricular ejection time in which blood in the left ventricle is ejected to the aorta after the aortic valve is opened.

The electrocardiogram data can be measured by electrocardiography (ECG) with electrodes or by photoplethysmography (PPG).

The electrocardiogram data includes any one or a combination of the breathing rate, the heart rate, the RR interval, the standard deviation of the RR interval, the MxDMn ratio, the power spectrum in a low frequency band, the power spectrum in a high frequency band, the heart rate variation indicator LF/HF, and the total power. The RR interval is the interval from a QRS wave to the next QRS wave in the electrocardiogram. The MxDMn ratio is the ratio of the longest RR interval and the shortest RR interval in a time period and is an index of irregular heartbeats. The total power is a calculated value of the total power of the power spectrum at the frequency of 0 to 0.4 Hz (VLF, LF, HF) in a measurement of two minutes. This value reflects the entire autonomic nerve activity dominated by sympathetic nerve activity.

The high-frequency power spectrum ratio (0.1875 to 0.50 Hz; HF), the low-frequency power spectrum ratio (0.05 to 0.1875 Hz; LF), the LF/HF ratio, and the very-low-frequency power spectrum ratio (0 to 0.05 Hz; VLF) can be calculated by calculating the power spectrum density based on the electrocardiogram.

The biological impedance (conductance) can be measured by, for example, generating small current flow between two electrodes among electrodes at the six sites of the legs, the hands, and the right and left foreheads. When current flows between two of the electrodes at the six sites, (1) anode/cathode conductance (μS), (2) cathode/anode conductance (μS), (3) the difference (delta SCRA-SCRC) between the conductance measured in (1) above and the conductance measured in (2) above, and (4) electric conductivity (μS/m) can be measured. In addition, the muscle mass, the body fat amount, the total moisture content, the phase angle, and the resistance value can be simultaneously measured. In addition, the dielectric constant (μSi) can be measured for cases of conduction between the right hand and the left hand and between the right forehead and the left forehead. The biological impedance (conductance) is preferably measured by using 22 conduction patterns with the electrodes at the six sites.

The biological impedance includes any one or a combination of the body fat amount (kg), the body fat amount (%), the lean body weight, the lean body rate, the muscle mass, the total moisture content (kg), the total moisture content (%), the in-cell moisture content (%), the cardiac output, 1 forehead left-side-2 left hand/SCR A, 1 forehead left-side-2 left hand/delta SCR C-SCR A, 5 left hand-6 left foot/SCR A, 5 left hand-6 left foot/delta SCR C-SCR A, 13 left foot-14 right foot/SCR C, 13 left foot-14 right foot/SCR A, 15 right hand-16 forehead left-side/delta SCR C-SCR A, 15 right hand-16 forehead left-side SCR C, 19 right foot-20 left hand/delta SCR C-SCR A, ESG 2+4+15+17 (μS/m), ESG 6+13+19(%), ESG 6+8+19+21(%), ESG 6+8+19+21 (μS/m), ESG 9+10 (μS/m), ESG 9+10(%), the left-foot conductance, R (Ω), the phase angle, the dielectric constant through a forehead path, forehead-path electric conductivity (9), the dielectric constant through a hand-to-hand path, hand-tohand electric conductivity (11, 12), and the single-output amount (cardiac output/heart rate).

SCR stands for skin conductance response, and ESG stands for electroscangram. The symbol "+" in ESG 2+4+15+17 indicates electrodes attached to the body and used for measurement. For example, ESG 2+4+15+17 means the average of conductance values measured at the left hand when conduction is made from the left hand to the left forehead, the right hand when conduction is made from the right hand to the right forehead, the right hand when conduction is made from the right hand to the left forehead, and the left hand when conduction is made from the left hand to the right forehead as illustrated in FIG. 2. Detailed description of these conductance values is provided in Non Patent Literature 1. Note that details of ESG (electroscangram) measurement methods are described in Non Patent Literatures 2 and 3.

The value "1 forehead left-side-2 left hand/SCR A" is conductance (or conductivity) measured through a path when current flows with "1 forehead left-side" at the cathode and "2 left hand" at the anode, and the value "5 left hand-6 left foot/delta SCR C-SCR A" is the difference between conductance values measured when conduction is made with "5 left hand" and "6 left foot" at the anode and the cathode and at the cathode and the anode.

The BMI and the blood pressure can be measured by a height-weight meter and a blood pressure meter. The non-invasive biological information may include an oxygen transport amount calculated based on SpO2 and the cardiac output.

The measured non-invasive biological information is output to the cholesterol risk estimation device 30 through a wired or wireless communication network. The biological information measurement device 20 may be a fixed measurement device or a portable measurement device such as a wearable terminal.

The cholesterol risk estimation device 30 includes a first acquisition unit 31, a second acquisition unit 32, a user data storage unit 33, a training data storage unit 34, a learning processing unit 35, an estimation model storage unit 36, an estimation processing unit 37, and an estimation data storage unit 38. The first acquisition unit 31 acquires the attribute information of the user from the terminal device 10. The second acquisition unit 32 acquires the non-invasive biological information of the user from the biological information measurement device 20.

The user data storage unit 33 stores the attribute information and the non-invasive biological information of the user, which are acquired from the first acquisition unit 31 and the second acquisition unit 32.

The training data storage unit 34 stores, as training data sets for machine learning, a plurality of training data sets each consisting of the attribute information and the non-invasive biological information acquired from a plurality of subjects in advance and sample examination information of cholesterol (LDL cholesterol or HDL cholesterol) obtained through a blood examination. Note that the sample examination information may further include examination information obtained from blood, urine, stool, or the like.

The learning processing unit 35 acquires the training data sets stored in the training data storage unit 34 and produces a cholesterol risk estimation model by using the training data sets. Specifically, when LDL cholesterol risk is estimated, the relation among the attribute information, the non-invasive biological information, and the LDL cholesterol risk is learned by machine learning with each acquired training data set by gradient boosting such as XGBoost. When HDL cholesterol risk is estimated, each acquired training data set is standardized or normalized and the relation among the attribute information, the non-invasive biological information, and the HDL cholesterol risk is learned by machine learning by logistic regression.

The estimation model storage unit 36 stores the cholesterol risk estimation model generated by the learning processing unit 35. The non-invasive biological information includes any one or a combination of BMI, blood pressure, pulse wave data, electrocardiogram data, and biological impedance. In addition, the oxygen saturation (SpO2) is included as necessary.

The estimation processing unit 37 estimates the cholesterol risk of the user based on the attribute information and/or the non-invasive biological information of the predetermined user by using the estimation model generated by the learning processing unit 35. Then, the cholesterol risk estimated value is stored in the estimation data storage unit 38.

The display device 39 can display the cholesterol risk estimated value together with the attribute information and the non-invasive biological information of the user. Note that these pieces of data may be displayed on the terminal device 10 possessed by the user.

<Device Hardware Configuration>

Figure 3:
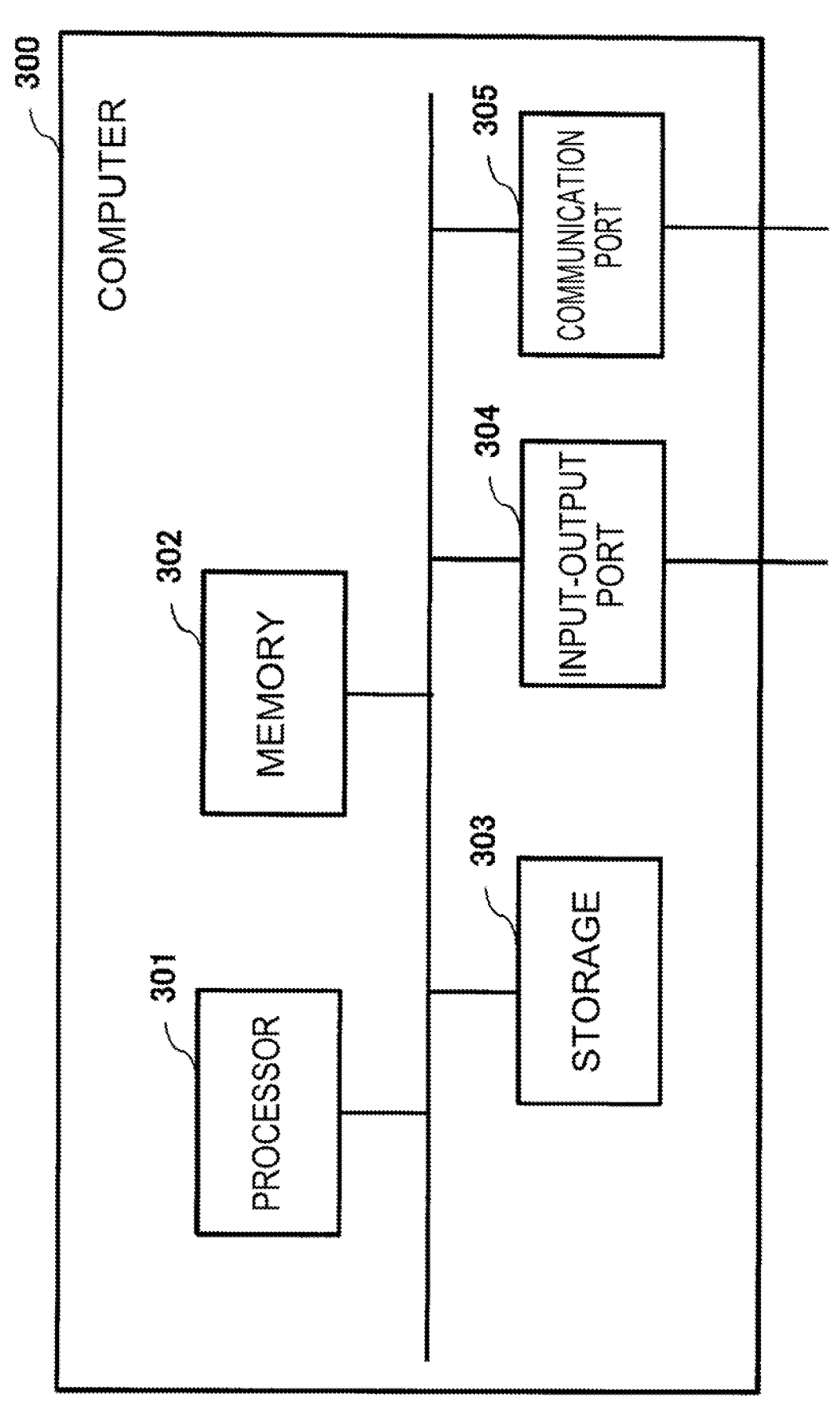
FIG. 3 is a hardware configuration diagram of a cholesterol risk estimation device.

FIG. 3 is a hardware configuration diagram of the cholesterol risk estimation device 30. As illustrated in FIG. 3, the cholesterol risk estimation device 30 is configured as a computer 300 including one or a plurality of processors 301, a memory 302, a storage 303, an input-output port 304, and a communication port 305. Each processor 301 performs processing related to cholesterol estimation according to the present embodiment by executing a computer program. The memory 302 temporarily stores a computer program and a calculation result of the computer program. The storage 303 stores a computer program configured to execute processing by the cholesterol risk estimation device 30. The storage 303 may be any computer-readable storage and may be, for example, various kinds of recording media such as a magnetic disk, an optical disk, a random-access memory, a flash memory, and a read-only memory. The input-output port 304 performs inputting of information from the terminal device 10 and the biological information measurement device 20 and outputting of a cholesterol estimated value to the display device 39. The communication port 305 transmits and receives data to and from a non-illustrated information terminal such as another computer. Communication may be performed by wireless and wired communication methods.

Note that the cholesterol risk estimation device 30 may be implemented by a commercially available desktop PC or notebook PC, and a time taken for calculation of a cholesterol risk estimated value using an estimation model is several seconds.

Note that the first acquisition unit 31, the second acquisition unit 32, the learning processing unit 35, the estimation processing unit 37, and the like described above function at the processor 301 of the cholesterol risk estimation device 30 when operating.

It is possible to perform cholesterol estimation without performing blood examination, by generating a cholesterol estimation model by machine learning based on non-invasive biological data including the body mass index (BMI), the blood pressure, the pulse wave data, the electrocardiogram data, the biological impedance, and the like.

As described below, it is also possible to determine whether the cholesterol is normal even when the number of pieces of data included in the non-invasive biological data is limited.

<Generation of LDL Cholesterol Risk Estimation Model by Machine Learning>

FIG. 4 is a flowchart illustrating an execution procedure of generation of the LDL cholesterol risk estimation model by machine learning.

At step ST101, the learning processing unit 35 performs preprocessing of input data (for example, the above-described training data set). Specifically, for LDL cholesterol obtained through a blood examination, the learning processing unit 35 converts the LDL cholesterol lower than 120 mg/dl into "0" (no risk is present) and the LDL cholesterol equal to or higher than 120 mg/dl into "1" (risk is present). When the number of subjects classified as "0" and the number of subjects classified as "1" are deviated and unbalanced, the learning processing unit 35 may apply SMOTE (Chawla, N V. et al. 2002) to learning data to artificially generate training samples. Specifically, a label (for example, above-described "0" or "1") indicating existence of the LDL cholesterol risk may be provided to each input data (training data set) based on the measured value of LDL cholesterol obtained through a blood examination. Then, when the difference between the number of labels with the LDL cholesterol risk (label "1") and the number of labels without the LDL cholesterol risk (label "0") is equal to or larger than a predetermined value, the number of pieces of sample data in the training data set may be increased (generated) to reduce the difference.

At step ST102, the learning processing unit 35 performs machine learning by a gradient boosting decision tree. Software libraries such as XGBoost, CatBoost, and Light-BGM may be used in machine learning by the gradient boosting decision tree.

The risk value (0: no risk is present or 1: risk is present) obtained by comparing the LDL cholesterol value obtained through a blood examination with a predetermined threshold value was compared with the LDL cholesterol risk value estimated by machine learning, and parameters (max_depth, subsample, colsample_bytree, and learning_rate) of XGBoost were adjusted to obtain the maximum f1 score, thereby generating an estimation model. The parameter "max_depth" represents the depth of a decision tree, the parameter "subsample" represents the ratio of samples randomly extracted at each tree, the parameter "colsample_bytree" represents the ratio of columns randomly extracted at each tree, and the parameter "learning_rate" represents the learning rate. The adjustment was performed with "max_depth" of 1 to 10, "subsample" of 0.1 to 1.0, "colsample_bytree" of 0.3 to 1.0, and "learning_rate" of 0.1 to 0.7.

The learning processing unit 35 stores the LDL cholesterol risk estimation model generated by the above-described learning processing in the estimation model storage unit 36.

Note that the above-described machine learning algorithm is exemplary and the present invention is not limited thereto.

<Estimation of LDL Cholesterol Risk Using LDL Cholesterol Risk Estimation Model>

As illustrated in FIG. 5, at step ST201, the first acquisition unit 31 of the cholesterol risk estimation device 30 acquires the attribute information of the user from the terminal device 10. At step ST202, the second acquisition unit 32 of the cholesterol risk estimation device 30 acquires the non-invasive biological information of the user. Then, the attribute information and the non-invasive biological information of the user are stored in the user data storage unit 33. Then at step ST203, the estimation processing unit 37 calculates probability that the user belongs to class 0 (no risk is present) or class 1 (risk is present), in other words, the LDL the cholesterol risk estimated value by using the LDL cholesterol risk estimation model stored in the estimation model storage unit 36. At step ST204, the calculated LDL cholesterol risk estimated value is stored in the estimation data storage unit 38, and at step ST205, the LDL cholesterol risk estimated value is output to and displayed on an external terminal such as the display device 39.

<Generation of HDL Cholesterol Risk Estimation Model by Machine Learning>

FIG. 6 is a flowchart illustrating an execution procedure of generation of the HDL cholesterol risk estimation model by machine learning.

At step ST301, the learning processing unit 35 performs preprocessing of input data. Specifically, for HDL cholesterol obtained through a blood examination, the learning processing unit 35 converts the HDL cholesterol equal to or higher than 40 mg/dl into "0" (no risk is present) and the HDL cholesterol lower than 40 mg/dl into "1" (risk is present). When the number of subjects classified as "0" and the number of subjects classified as "1" are deviated and unbalanced, the learning processing unit 35 may apply SMOTE (Chawla, N V. et al. 2002) to learning data to artificially generate training samples. Specifically, a label (for example, above-described "0" or "1") indicating existence of the HDL cholesterol risk may be provided to each input data (training data set) based on the measured value of HDL cholesterol obtained through a blood examination. Then, when the difference between the number of labels with the HDL cholesterol risk (label "1") and the number of labels without the HDL cholesterol risk (label "0") is equal to or larger than a predetermined value, the number of pieces of sample data in the training data set may be increased (generated) to reduce the difference. In addition, data standardization and normalization are performed.

At step ST302, the learning processing unit 35 performs machine learning by the logistic regression. For example, Logistic Regression provided in a Python open-source machine learning library Scikit-learn may be used for machine learning by the logistic regression. The number of dimensions may be reduced by primary component analysis as necessary.

The risk value (0: no risk is present or 1: risk is present) obtained by comparing the HDL cholesterol value obtained through a blood examination with a predetermined threshold value was compared with the HDL cholesterol risk value estimated by machine learning, and parameters (C, regularization method, max_iter, and solber) of Logistic Regression were adjusted to obtain the maximum f1 score, thereby generating the HDL cholesterol risk estimation model. The parameter "C" is a tradeoff parameter that determines the strength of regularization, and the strength of regularization is weaker as the value of the parameter is larger. The parameter "regularization method" means L1 regularization or L2 regularization to be selected. The parameter "max_iter" is the maximum number of iterations of learning. The parameter "solber" selects a convergence method (for example, the L-BFGS method, the Newton CG method, liblinear, sag, or saga) that minimizes the cross-entropy loss. Note that the liblinear method was selected in Examples 2 and 3 below.

The learning processing unit 35 stores the HDL cholesterol risk estimation model generated by the above-described learning processing in the estimation model storage unit 36.

Note that the above-described machine learning algorithm is exemplary and the present invention is not limited thereto.

<Estimation of HDL Cholesterol Risk Using HDL Cholesterol Risk Estimation Model>

As illustrated in FIG. 7, at step ST401, the first acquisition unit 31 of the cholesterol risk estimation device 30 acquires the attribute information of the user from the terminal device 10. At step ST402, the second acquisition unit 32 of the cholesterol risk estimation device 30 acquires the non-invasive biological information of the user. Then, the attribute information and the non-invasive biological information of the user are stored in the user data storage unit 33. Then at step ST403, the estimation processing unit 37 calculates probability that the user belongs to class 0 (no risk is present) or class 1 (risk is present), in other words, a HDL cholesterol risk estimated value by using the HDL cholesterol risk estimation model stored in the estimation model storage unit 36. At step ST404, the calculated HDL cholesterol risk estimated value is stored in the estimation data storage unit 38. At step ST405, the HDL cholesterol risk estimated value is output to an external terminal such as the display device 39 and displayed.

<Examples (LDL Cholesterol Risk Estimation)>

Examples of LDL cholesterol risk estimation will be described below. However, aspects of the LDL cholesterol risk estimation in the present invention are not limited to the examples below.

The attribute information includes any one or a combination of ID, full name, age, and sex, and the non-invasive biological information includes any one or a combination of the BMI, the blood pressure, the pulse wave data, the electrocardiogram data, the biological impedance, and the oxygen saturation (SpO2). Height and weight as calculation references of the BMI were measured by a height meter and a weight meter, respectively, and the blood pressure was measured by a blood pressure meter. The pulse wave data, the electrocardiogram data, the biological impedance, and the oxygen saturation (SpO2) were measured by ES-TECK BC-3 (Ryobi Systems Co., Ltd.). Note that a pulse wave meter, an electrocardiogram meter, an impedance measurement device, and a pulse oximeter that are commercially available may be used in combination in place of ES-TECK BC-3. The above-described non-invasive biological information may be acquired by using a predetermined wearable terminal.

The biological impedance (conductance) was measured by generating small current flow between two electrodes among electrodes at the six sites of the feet, the hands, and the right and left foreheads. Voltage and current were 1.28 V and 200 µA, respectively, and the conductance was measured for 32 milliseconds per second. Current was caused to flow between two of the electrodes at the six sites to measure (1) anode/cathode conductance (µS), (2) cathode/anode conductance (µS), (3) the difference (delta SCRA-SCRC) between the conductance measured in (1) above and the conductance measured in (2) above, and (4) electric conductivity (µS/m).

In addition, the muscle mass, the body fat amount, the total moisture content, the phase angle, and the resistance value were measured, and the dielectric constant (µSi) was measured for cases of conduction between the right hand and the left hand and between the right forehead and the left forehead.

The pulse wave data, the electrocardiogram data, the biological impedance, and the oxygen saturation (SpO2) were measured for two minutes by using ES-TECK BC-3 for each subject. At the measurement, a device having functions of an electrocardiogram, a pulse wave meter, and a pulse oximeter was mounted on the left hand forefinger of each subject, two electrodes were mounted on the forehead, and the hands and feet were placed on electrode plates while the subject was seated on a chair.

<Learning Model 1>

With a learning model 1, machine learning by the gradient boosting decision tree was performed as illustrated in FIG. 4.

In this case, data described below was selected and used as the attribute information and non-invasive biological data. (A) the attribute information: age, (B) the non-invasive biological data: the blood pressure, the diastolic blood pressure, pulse wave data, elasticity index, electrocardiogram data, the heart rate, the standard deviation of the RR interval, the biological impedance, the body fat amount (kg), the muscle mass, the total moisture content (%), the cardiac output, 5 left hand-6 left foot/SCRA, ESG 2+4+15+17 (µS/m), ESG 9+10 (µS/m), ESG 9+10(%), and R (Ω).

ESG 9+10 is the average of impedance values measured at the sites illustrated in FIG. 2. The unit [µS/m] is the unit of a measured average, and the unit [%] is a value obtained by scaling the measured average into the range of normally measured values.

In addition, the cardiac output included in the biological impedance and the oxygen transport amount estimated from the oxygen saturation (SpO2) are included in the non-invasive biological data.

Example 1

In Example 1, the LDL cholesterol risk estimation model was generated through machine learning of the above-described learning model 1 by using (1) the attribute information, (2) the non-invasive biological information measured by a height-weight meter, a blood pressure meter, and ES-TECK BC-3, and (3) a training data set of LDL cholesterol obtained through a blood examination performed on the same day as the non-invasive biological information measurement for 712 subjects.

Then, an estimation result was evaluated by using an ROC_AUC curve for the estimation accuracy of the LDL cholesterol risk estimation model. As a result, ROC_AUC was 0.71, which exceeds 0.7 indicating favorable classification. The ROC_AUC curve of the estimation result in Example 1 is illustrated in FIG. 8.

<Examples (HDL Cholesterol Risk Estimation)>

Examples of HDL cholesterol risk estimation will be described below. However, aspects of the HDL cholesterol risk estimation in the present invention are not limited to the examples below.

The attribute information includes any one or a combination of ID, full name, age, and sex, and the non-invasive biological information includes any one or a combination of the BMI, the blood pressure, the pulse wave data, the electrocardiogram data, the biological impedance, and the oxygen saturation (SpO2). Height and weight as calculation references of the BMI were measured by a height meter and a weight meter, respectively, and the blood pressure was measured by a blood pressure meter. The pulse wave data, the electrocardiogram data, the biological impedance, and the oxygen saturation (SpO2) were measured by ES-TECK BC-3 (Ryobi Systems Co., Ltd.). Note that a pulse wave meter, an electrocardiogram meter, an impedance measurement device, and a pulse oximeter that are commercially available may be used in combination in place of ES-TECK BC-3. The above-described non-invasive biological information may be acquired by using a predetermined wearable terminal.

The biological impedance (conductance) was measured by generating small current flow between two electrodes among electrodes at the six sites of the feet, the hands, and the right and left foreheads. Voltage and current were 1.28 V and 200 μA, and the conductance was measured for 32 milliseconds per second. Current was caused to flow between two of the electrodes at the six sites to measure (1) anode/cathode conductance (μS), (2) cathode/anode conductance (μS), (3) the difference (delta SCRA-SCRC) between the conductance measured in (1) above and the conductance measured in (2) above, and (4) electric conductivity (μS/m).

In addition, the muscle mass, the body fat amount, the total moisture content, the phase angle, and the resistance value were measured, and the dielectric constant (μSi) was measured for cases of conduction between the right hand and the left hand and between the right forehead and the left forehead.

The pulse wave data, the electrocardiogram data, the biological impedance, and the oxygen saturation (SpO2) were measured for two minutes by using ES-TECK BC-3 for each subject. At the measurement, a device having functions of an electrocardiogram, a pulse wave meter, and a pulse oximeter was mounted on the left hand forefinger of each subject, two electrodes were mounted on the forehead, and the hands and feet were placed on electrode plates while the subject was seated on a chair.

<Learning Model 2>

With a learning model 2, machine learning by the logistic regression was performed as illustrated in FIG. 6.

In this case, data described below was selected and used as the attribute information and the non-invasive biological data. (A) the attribute information: sex, (B) the non-invasive biological data: the blood pressure, the pulse pressure, pulse wave data, the peripheral vascular resistance, pulse, e/a, the second derivative of photoplethysmogram aging index, electrocardiogram data, LF/HF, the biological impedance, the lean body rate (%), 15 right hand-16 forehead left-side/SCRC, ESG 9+10 (μS/m), the dielectric constant through a forehead path, pulse oximeter, and SpO2.

In addition, the cardiac output included in the biological impedance, the oxygen transport amount estimated from the oxygen saturation (SpO2), and the pulse pressure/pulse calculated from pulse and the pulse pressure are included in the non-invasive biological data.

<Learning Model 3>

With a learning model 3, machine learning by the logistic regression was performed as illustrated in FIG. 6.

In this case, data described below was selected and used as the attribute information and the non-invasive biological data. (A) the attribute information: sex, (B) the non-invasive biological data: the BMI, electrocardiogram data, the RR interval, the biological impedance, the cardiac output, 13 left foot-14 right foot/SCRC, and R (Ω).

In addition, the cardiac output included in the biological impedance and the oxygen transport amount estimated from the oxygen saturation (SpO2) are included in the non-invasive biological data.

Example 2

In Example 2, the HDL cholesterol risk estimation model was generated through machine learning of the above-described learning model 2 by using (1) the attribute information, (2) the non-invasive biological information measured by a height-weight meter, a blood pressure meter, and ES-TECK BC-3, and (3) a training data set of HDL cholesterol obtained through a blood examination performed on the same day as the non-invasive biological information measurement for 321 subjects.

Then, an estimation result was evaluated by using an ROC_AUC curve for the estimation accuracy of the HDL cholesterol risk estimation model. As a result, ROC_AUC was 0.78, which exceeds 0.7 indicating favorable classification. The ROC_AUC curve of the estimation result in Example 2 is illustrated in FIG. 9.

Example 3

In Example 3, the HDL cholesterol risk estimation model was generated through machine learning of the above-described learning model 3 by using (1) attribute information, (2) the non-invasive biological information measured by a height-weight meter, a blood pressure meter, and ES-TECK BC-3, and (3) a training data set of HDL cholesterol obtained through a blood examination performed on the same day as the non-invasive biological information measurement for a total of 712 subjects.

Then, an estimation result was evaluated by using an ROC_AUC curve for the estimation accuracy of the HDL cholesterol risk estimation model. As a result, ROC_AUC was 0.87, which exceeds 0.8 indicating extremely favorable classification. The ROC_AUC curve of the estimation result in Example 3 is illustrated in FIG. 10.

(Modification)

In the above-described embodiment, the HDL cholesterol risk is estimated by using the learning model 2 or the learning model 3, but the HDL cholesterol risk may be estimated by using a plurality of learning models.

Accordingly, the HDL cholesterol risk can be estimated at higher accuracy than the HDL cholesterol risk is estimated by using one learning model.

In the above-described embodiment and examples, the estimation accuracy improves in some cases when the BMI is used for a learning model data set, and thus a functional component configured to estimate the BMI may be provided in a cholesterol risk estimation device.

The BMI is typically not acquired by a wearable terminal nor the like but is calculated based on a height and a weight input by the user. However, when the BMI is estimated, the above-described cholesterol risk can be acquired by only acquiring biological information, which improves convenience for the user.

The BMI estimation is not limited to a particular method, but for example, it is known that the BMI is correlated with inclination of the abdominal region (predetermined position) of the user. Thus, for example, a predetermined acceleration sensor may be provided on the abdominal region of the user (or a wrist-band wearable terminal or the like including an acceleration sensor may be placed on the abdominal region), and the BMI may be estimated by calculating the inclination of the abdominal region based on data output from the acceleration sensor.

Similarly to the above description, the pulse wave data or the oxygen saturation may be estimated by using a wrist-band wearable terminal or the like including a pulse wave sensor or a blood oxygen level sensor.

Similarly to the above description, the blood pressure may be estimated by using a wrist-band wearable terminal or the like. Since it is known that the blood pressure is correlated with the speed of a pulse wave transferred through an artery by heartbeat, the blood pressure may be estimated by using a predetermined sensor configured to measure the speed of a pulse wave transferred through an artery by heartbeat.

Similarly to the above description, the electrocardiogram data may be estimated by using a wrist-band wearable terminal or the like. For example, the electrocardiogram data may be estimated based on data obtained from an electrode provided on a surface on a side opposite a display surface of a wrist-band wearable terminal and an electrode provided on the display surface side. Specifically, the electrocardiogram data may be estimated based on data obtained when the wrist of a hand (for example, the left hand) on which the wrist-band wearable terminal is mounted contacts the electrode provided on the opposite surface and a fingertip of a hand (for example, the right hand) opposite to the mounted hand contacts the electrode provided on the display surface side.

Similarly to the above description, the biological impedance may be estimated by using a wrist-band wearable terminal or the like including various electrodes. For example, the biological impedance may be estimated based on biological information obtained from the thoracic region and a wrist by using a wrist-band wearable terminal or the like.

Note that the above-described estimation target biological information (at least one piece or more of biological information among the BMI, the blood pressure, the pulse wave data, the electrocardiogram data, the biological impedance, and the oxygen saturation) may be estimated by using a classifier generated by using various kinds of machine learning algorithms with, as teacher data, biological information that is acquirable by a wearable terminal and the above-described estimation target biological information.

In this case, the above-described second acquisition unit may acquire the estimated biological information.
(Other)

For example, the series of above-described processing may be executed by hardware or software. In other words, the above-described functional configurations are merely exemplary and not particularly limited. Specifically, it suffices that the functionality of executing the entire series of above-described processing is provided at an information processing system, and which functional blocks are used to achieve the functionality is not particularly limited to the above-described example. Places at which functional blocks exist are not particularly limited to those in FIG. 1 but may be optional. For example, functional blocks of a server may be transferred to another terminal or device. Functional blocks of another terminal or device may be transferred to a server or the like. Each functional block may be configured by hardware only, by software only, or by combination thereof.

When the series of processing is executed by software, computer programs constituting the software are installed on a computer or the like from a network or a recording medium. The computer may be a computer incorporated in dedicated hardware. Alternatively, the computer may be a computer capable of executing various functions with various computer programs installed thereon, such as a server or a general-purpose smartphone or personal computer.

A recording medium including such computer programs is not only configured as a non-illustrated removable media distributed separately from the device body to provide the computer programs to a user or the like, but also configured as, for example, a recording medium incorporated in the device body in advance and provided to the user or the like. The computer programs can be distributed through a network, and thus the recording medium may be mounted on or accessible from a computer connected or connectable to the network.

Note that, in the present specification, steps representing the computer programs recorded in the recording medium include not only processing performed in a temporally sequential manner in accordance with an order but also processing not necessarily processed in a temporally sequential manner but executed in parallel or individually. In the present specification, system terms mean those of an overall device including a plurality of devices, a plurality of units, or the like.

REFERENCE SIGNS LIST 1 cholesterol risk estimation system
10 terminal device
20 biological information measurement device
30 cholesterol risk estimation device
31 first acquisition unit
32 second acquisition unit
33 user data storage unit
34 training data storage unit
35 learning processing unit
36 estimation model storage unit
37 estimation processing unit
38 estimation data storage unit
39 display device
300 computer
301 processor
302 memory
303 storage
304 input-output port
305 communication port

The invention claimed is:
1. A cholesterol risk estimation device comprising:
a memory storing instructions; and
at least one processor configured to execute the instructions;
wherein, by executing the instructions, the at least one processor is configured to control:
a training data storage unit to store a training data set;
a learning processing unit to:
provide labels indicating existence of the cholesterol risk to the training data set based on a blood-measured cholesterol value, and when a difference between a number of pieces of data with the cholesterol risk and a number of pieces of data without the cholesterol risk among the labels is equal to or larger than a predetermined value, the learning processing unit increases a number of pieces of sample data in the training data set to reduce the difference, and
generate a cholesterol risk estimation model by machine learning based on the processed training data set;
an information acquisition unit to acquire attribute information and non-invasive biological information of a predetermined user, the attribute information including age of the predetermined user, and the non-invasive biological information including:
blood pressure including diastolic blood pressure,
pulse wave data including an elasticity index,
electrocardiogram data including a heart rate and a standard deviation of an RR interval, and
a biological impedance of the predetermined user including:

a body fat amount (kg), muscle mass, total moisture content (%), cardiac output, a conductance value measured when current flows through a path with a left hand at a cathode and a left foot at an anode, an average of conductance values measured at the left hand of the predetermined user when conduction is made from the left hand to a left forehead of the predetermined user, a right hand of the predetermined user when conduction is made from the right hand to a right forehead of the predetermined user, the right hand when conduction is made from the right hand to the left forehead, and the left hand when conduction is made from the left hand to the right forehead of the predetermined user (μS/m), an average of impedance values measured at the left forehead and the left hand of the predetermined user (μS/m), an average of impedance values measured at the left forehead and the left hand of the predetermined user (%), and

R (Ω);

a user data storage unit to store the attribute information and the non-invasive biological information of the predetermined user;

an estimation model storage unit to store the cholesterol risk estimation model; and an estimation processing unit to:

input, from the user data storage unit, the attribute information and the non-invasive biological information of the predetermined user into the cholesterol risk estimation model, and output, from the cholesterol risk estimation model, a cholesterol risk estimated value of the predetermined user.

2. The cholesterol risk estimation device according to claim 1, wherein estimation accuracy of the cholesterol risk estimated value is accuracy at which risk presence can be classified with ROC_AUC of 0.7 or larger.

3. The cholesterol risk estimation device according to claim 1, wherein the training data set includes attribute information, non-invasive biological information, and a blood-measured cholesterol measured value of a subject.

4. The cholesterol risk estimation device according to claim 3, wherein the non-invasive biological information further includes oxygen saturation (SpO2).

5. The cholesterol risk estimation device according to claim 1, wherein the at least one processor is further configured to control:

the learning processing unit to generate a first cholesterol risk estimation model and a second cholesterol risk estimation model by machine learning based on each of training data sets of different kinds, and the estimation processing unit to calculate the cholesterol risk estimated value of the predetermined user by using the first cholesterol risk estimation model and the second cholesterol risk estimation model.

6. The cholesterol risk estimation device according to claim 1, wherein the at least one processor is further configured to control:

a biological information estimation unit to estimate at least one piece or more of biological information among BMI, blood pressure, pulse wave data, electrocardiogram data, biological impedance, and oxygen saturation included in the biological information, and the information acquisition unit to acquire, as the biological information of the predetermined user, the biological information estimated by the biological information estimation unit.

7. A non-invasive cholesterol risk estimation system comprising:

the cholesterol risk estimation device according to claim 1; and a biological information measurement device.

8. The cholesterol risk estimation device according to claim 2, wherein the training data set includes attribute information, non-invasive biological information, and a blood-measured cholesterol measured value of a subject.

9. The cholesterol risk estimation device according to claim 1, wherein the non-invasive biological includes information that is not acquired through insertion of an instrument into the skin or an opening part of the predetermined user.

10. The cholesterol risk estimation device according to claim 1, wherein the at least one processor is further configured to control a display device to display the cholesterol risk estimated value together with the attribute information and the non-invasive biological information of the predetermined user.

11. A cholesterol risk estimation method comprising:

a step of storing a training data set including attribute information, non-invasive biological information, and a blood-measured cholesterol measured value of a subject;

a step of generating a cholesterol risk estimation model by machine learning based on the training data set, comprising:

providing labels indicating existence of a cholesterol risk to the training data set based on a blood-measured cholesterol value, based on a difference between a number of pieces of data with the cholesterol risk and a number of pieces of data without the cholesterol risk among the labels is equal to or larger than a predetermined value, increasing a number of pieces of sample data in the training data set to reduce the difference, and generating the cholesterol risk estimation model by machine learning based on the processed training data set;

a step of acquiring attribute information and non-invasive biological information of a predetermined user, the attribute information including age of the predetermined user, and the non-invasive biological information including:

blood pressure including diastolic blood pressure, pulse wave data including an elasticity index, electrocardiogram data including a heart rate and a standard deviation of an RR interval, and a biological impedance of the predetermined user including:

a body fat amount (kg), muscle mass, total moisture content (%), a cardiac output, a conductance value measured when current flows through a path with a left hand at a cathode and a left foot at an anode, an average of conductance values measured at the left hand of the predetermined user when conduction is made from the left hand to a left forehead of the predetermined user, a right hand of the predetermined user when conduction is made from the right hand to a right forehead of the predetermined user, the right hand when conduction is made from the right hand to the left forehead, and the left hand when conduction is made from the left hand to the right forehead of the predetermined user (μS/m), an average of impedance values measured at the left forehead and the left hand of the predetermined user (μS/m), an average of impedance values measured at the left forehead and the left hand of the predetermined user (%), and

R (Ω);

a step of storing, in a user data storage unit, the attribute information and the non-invasive biological information of the predetermined user; and a step of inputting, from the user data storage unit, the attribute information and the non-invasive biological information of the predetermined user into the cholesterol risk estimation model, and outputting, from the cholesterol risk estimation model, a cholesterol risk estimated value of the predetermined user.

12. A non-transitory computer-readable storage medium storing a computer program which, when executed by a computer, cause the computer to execute:

a step of storing a training data set including attribute information, non-invasive biological information, and a blood-measured cholesterol measured value of a subject;

a step of generating a cholesterol risk estimation model by machine learning based on the training data set, comprising:

providing labels indicating existence of a cholesterol risk to the training data set based on a blood-measured cholesterol value, based on a difference between a number of pieces of data with the cholesterol risk and a number of pieces of data without the cholesterol risk among the labels is equal to or larger than a predetermined value, increasing a number of pieces of sample data in the training data set to reduce the difference, and generating the cholesterol risk estimation model by machine learning based on the processed training data set;

a step of acquiring attribute information and non-invasive biological information of a predetermined user, the attribute information including age of the predetermined user, and the non-invasive biological information including:

blood pressure including diastolic blood pressure, pulse wave data including an elasticity index, electrocardiogram data including a heart rate and a standard deviation of an RR interval, and a biological impedance of the predetermined user including:

a body fat amount (kg), muscle mass, total moisture content (%), cardiac output, a conductance value measured when current flows through a path with a left hand at a cathode and a left foot at an anode, an average of conductance values measured at the left hand of the predetermined user when conduction is made from the left hand to a left forehead of the predetermined user, a right hand of the predetermined user when conduction is made from the right hand to a right forehead of the predetermined user, the right hand when conduction is made from the right hand to the left forehead, and the left hand when conduction is made from the left hand to the right forehead of the predetermined user (μS/m), an average of impedance values measured at the left forehead and the left hand of the predetermined user (μS/m), an average of impedance values measured at the left forehead and the left hand of the predetermined user (%), and

R (Ω);

a step of storing, in a user data storage unit, the attribute information and the non-invasive biological information of the predetermined user; and a step of inputting, from the user data storage unit, the attribute information and the non-invasive biological information of the predetermined user into the cholesterol risk estimation model, and outputting, from the cholesterol risk estimation model, a cholesterol risk estimated value of the predetermined user.

\* \* \* \* \*